United States Patent [19]

Peter et al.

[11] 4,100,111

[45] Jul. 11, 1978

[54] CURABLE MIXTURES

[75] Inventors: Heinz Peter, Rheinfelden, Switzerland; Dieter Reinehr, Wittlingen, Germany; Eduard Troxler, Basel, Switzerland

[73] Assignee: Ciba-Geigy Corporation, Ardsley, N.Y.

[21] Appl. No.: 626,896

[22] Filed: Oct. 29, 1975

[30] Foreign Application Priority Data

Nov. 7, 1974 [CH] Switzerland .................. 14891/74

[51] Int. Cl.$^2$ ............................................. C08G 59/50
[52] U.S. Cl. .................................. 528/116; 260/152; 260/239 BC; 260/570.5 P; 260/563 P; 260/583 P
[58] Field of Search ............ 260/47 EN, 59 EP, 2 N, 260/570.5 P, 583 P, 563 P, 78.41

[56] References Cited

U.S. PATENT DOCUMENTS

| 3,303,165 | 2/1967 | Wallis et al. | 260/47 |
| 3,361,821 | 2/1968 | Wallis et al. | 260/583 |
| 3,563,959 | 2/1971 | Schade et al. | 260/78 |
| 3,707,563 | 12/1972 | Pikl | 260/583 P |

FOREIGN PATENT DOCUMENTS 737,423  9/1955  United Kingdom.

OTHER PUBLICATIONS

Yano et al., "Mechanism of Rate of Setting", Chem. Abstr. 75, 64795u (1971).

*Primary Examiner*—Harold D. Anderson
*Assistant Examiner*—E. A. Nielsen
*Attorney, Agent, or Firm*—Vincent J. Cavalieri

[57] ABSTRACT

The invention relates to curable mixtures which contain 1,10-substituted 1,10-diaminodecanes, as the curing agents, new 1,10-substituted 1,10-diaminodecanes and a process for the manufacture of the latter.

The new 1,10-diaminodecanes are manufactured by catalytic hydrogenation of corresponding 3,12-substituted 1,2-diazo-1,5,9-cyclododecatrienes in the presence of an inert organic solvent, while raising the temperature to at least 120° C.

14 Claims, No Drawings

CURABLE MIXTURES

The present invention relates to curable mixtures which contain 1,10-substituted 1,10-diaminodecanes as the curing agents, new, substituted 1,10-diaminodecanes and a process for their manufacture.

The curable mixtures according to the invention are suitable for the manufacture of mouldings, impregnated materials, coatings, lacquers and sealings and are characterised in that they contain (a) a polyepoxide and (b), as the curing agent, at least one 1,10-diaminodecane of the formula I

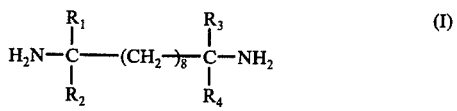

wherein $R_1$ and $R_3$ independently of one another represent an unsubstituted or substituted alkyl, cycloalkyl, aralkyl, phenyl or naphthyl group and $R_2$ and $R_4$ independently of one another represent hydrogen or an unsubstituted or substituted alkyl, cycloalkyl, aralkyl, phenyl or naphthyl group or $R_1$ and $R_2$ and/or $R_3$ and $R_4$, conjointly with the carbon atom to which they are linked, form an unsubstituted or substituted 5-membered to 12-membered alkylene or oxaalkylene ring.

In principle, any desired groups which cannot be hydrogenated under the reaction conditions, such as alkyl, alkoxy, alkylamino, N,N-dialkylamino, cyclic ether and cycloalkyl groups, are possible as substituents on alkyl, cycloalkyl, aralkyl, phenyl and naphthyl groups represented by $R_1$ to $R_4$.

Possible alkyl groups $R_1$ to $R_4$ are above all straight-chain or branched groups having 1-18, preferably 1-8, carbon atoms. If such groups are substituted, they are, for example, alkoxy, alkylamino or N,N-dialkylamino groups having in each case 1-4, particularly 1 or 2, carbon atoms in the alkoxy or alkyl portions, cyclic ether groups having 3 or 4 carbon atoms, or cycloalkyl groups having 5-8, preferably 5 or 6, ring carbon atoms. The following should be mentioned as examples of alkyl groups $R_1$ to $R_4$ of this kind: methyl, ethyl, n-propyl, isopropyl, n-, sec.- and tert.-butyl, n-hexyl, n-heptyl, n-octyl, n-decyl, n-dodecyl, n-octadecyl, methoxyethyl, 2-ethoxyethyl, 2-methylaminoethyl, 3-N,N-diethylaminopropyl, 2-cyclohexylethyl, 2-furyl-(3)-ethyl and 3-pyranyl-(3)-propyl.

If cycloalkyl, aralkyl, phenyl or naphthyl groups represented by $R_1$ to $R_4$ are substituted, possible substituents are above all alkyl, alkoxy, alkylamino and N,N-dialkylamino groups having in each case 1-4, particularly 1 or 2, carbon atoms in the alkyl or alkoxy portions.

Cycloalkyl groups represented by $R_1$ to $R_4$ can be 1-nuclear or 2-nuclear and preferably have 5-12, particularly 5-10, ring carbon atoms.

The following examples should be mentioned: the cyclopentyl, 2-propylcyclopentyl, cyclohexyl, 4-methylcyclohexyl, 4-methoxycyclohexyl, 4-N,N-diethylaminocyclohexyl, cis- or trans-decahydronaphthyl, methylcycloheptyl, cyclooctyl and cyclododecyl groups.

Aralkyl groups represented by $R_1$ to $R_4$ preferably have 6-10 ring carbon atoms. Examples of such groups are: the benzyl, 2-phenylethyl, 1-methylnaphthyl, 4-methoxy and 4-methylbenzyl groups.

The following should be mentioned as examples of phenyl and naphthyl groups $R_1$ to $R_4$ according to the definition: the phenyl, 1-naphthyl, 2-naphthyl, 4-ethylphenyl, 3-methoxyphenyl, 4-n-propylaminophenyl, 3,4-dimethoxyphenyl and the 4-N,N-dimethylaminophenyl groups.

Alkylene or oxaalkylene rings which are formed by $R_1$ conjointly with $R_2$ and/or $R_3$ conjointly with $R_4$, can also be substituted, for example by alkyl or alkoxy groups having 1-4, particularly 1 or 2, carbon atoms. Thus $R_1$ and $R_2$ or $R_3$ and $R_4$ form, conjointly with the carbon atom to which they are linked, for example, a cyclopentyl, cyclohexyl, methylcyclohexyl, tetrahydrofuryl, 4-methyltetrahydrofuryl-3, tetrahydropyranyl, cycloheptyl, cyclooctyl, cyclodecyl or cyclododecyl ring.

Preferred 1,10-diaminodecanes are those of the formula I wherein $R_1$ and $R_3$ independently of one another represent an unsubstituted alkyl group having 1-18, particularly 1-8, carbon atoms, a 1-nuclear or 2-nuclear cycloalkyl group having 5-10 ring carbon atoms, which can be substituted by alkoxy, alkylamino or N,N-dialkylamino groups having in each case 1 or 2 carbon atoms in the alkoxy or alkyl portions, the benzyl or 2-phenylethyl group, an unsubstituted phenyl group or a phenyl group which is substituted by alkyl, alkoxy, alkylamino or N,N-dialkylamino groups having in each case 1 or 2 carbon atoms in the alkyl or alkoxy portions, or an unsubstituted naphthyl group, and $R_2$ and $R_4$ independently of one another represent hydrogen or one of the groups indicated above under $R_1$ and $R_3$, as well as compounds of the formula I wherein $R_1$ and $R_2$ and/or $R_3$ and $R_4$, conjointly with the carbon atom to which they are linked, form an unsubstituted 5-membered to 12-membered alkylene ring or an unsubstituted 5-membered or 6-membered oxaalkylene ring.

In accordance with a further preference, $R_1$ and $R_3$ as well as $R_2$ and $R_4$ each represent identical groups.

1,10-Diaminodecanes which are very particularly prefred are those of the formula I wherein $R_1$ and $R_3$ are identical and each represent an unsubstituted alkyl group having 1-8 carbon atoms or a 1-nuclear or 2-nuclear cycloalkyl group which has 5-10 ring carbon atoms, preferably cyclohexyl, cyclopentyl or cyclooctyl, and which is unsubstituted or substituted by alkoxy, alkylamino or N,N-dialkylamino groups having in each case 1 or 2 carbon atoms in the alkoxy or alkyl portions, and $R_2$ and $R_4$ are different and each represent hydrogen or an unsubstituted alkyl group having 1-8 carbon atoms.

The invention also relates to the new 1,10-diaminodecanes of the formual Ia

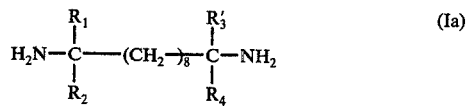

wherein $R_1$ represents an unsubstituted or substituted alkyl, cycloalkyl, aralkyl, phenyl or naphthyl group, $R_3'$ represents an unsubstitued or substituted alkyl, cycloalkyl, aralkyl or naphthyl group which corresponds to $R_3$, or represents a substituted phenyl group and $R_2$ and $R_4$ independently of one another represent hydrogen or an unsubstituted or substituted alkyl, cycloalkyl, aralkyl, phenyl or naphthyl group, or $R_1$ and $R_2$ and/or $R_3'$ and $R_4$, conjointly with the carbon atom to which they are linked, form an unsubstituted or substituted 5-membered to 12-membered alkylene or oxaalkylene ring.

In the above formula Ia, what has been said in the preceding text applies to $R_1$, $R_2$ and $R_4$ and to $R_3'$ as an alkyl, cycloalkyl, aralkyl or naphthyl group which corresponds to $R_3$, and to alkylene or oxaalkylene rings which are formed by $R_3'$ conjointly with $R_4$.

If $R_3'$ represents a substituted phenyl group, possible substituents are those mentioned above, particularly alkyl, alkoxy, alkylamino and N,N-dialkylamino groups having 1 or 2 carbon atoms in the alkyl or alkoxy portions.

The 1,10-diaminodecanes of the formula Ia according to the invention can be obtained by hydrogenating a compound of the formula II

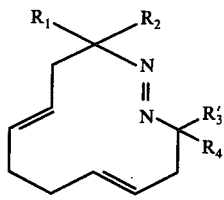

(II)

wherein what has been indicated under formula Ia applies to $R_1$, $R_2$, $R_3'$ and $R_4$, in the presence of an inert organic solvent, by catalytic means, in one or two stages and with the reaction temperature being raised to at least 120° C, to give a compound of the formula Ia.

In the course thereof, it is also possible, depending on the nature of the starting compound of the formula II, of the catalyst and/or of the reaction conditions, to hydrogenate phenyl groups or naphthyl groups which are represented by $R_1$, $R_2$, $R_3'$ and $R_4$ in formula II.

In the two-stage hydrogenation it is appropriate to proceed by hydrogenating a compound of the formula II at a temperature below 150° C to give a compound of the formula III

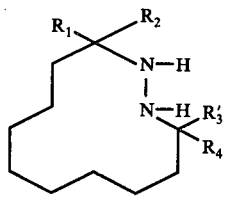

(III)

in the first stage, and subsequently to hydrogenate the compound of the formula III at elevated temperature and preferably with the addition of ammonia, to give a compound of the formula Ia.

1,10-Diaminodecanes of the formula Ia wherein $R_2$ and $R_4$ each represent hydrogen, can also be obtained by one-stage hydrogenation of corresponding starting compounds of the formula II at a temperature of at least 120° C.

Hydrogenation catalysts which are in themselves known can be used as the catalysts. These catalysts can be used in the customary forms, for example as finely divided powders, in colloidal form, as oxides or hydroxides or applied to suitable supporting materials, such as asbestos, pumice, kieselguhr, silica gel, silica, active charcoal or sulphates, carbonates or oxides of the metals of the II to VII group of the periodic system, particularly magnesium, calcium, barium, zinc, aluminum, iron and chromium.

For the one-stage hydrogenation and in the first phase of the two-stage hydrogenation, it is appropriate to use noble metal catalysts, such as platinum, rhodium, palladium, ruthenium and iridium catalysts, preferably rhodium/aluminium oxide or palladium-on-charcoal catalysts.

For the second phase in the two-stage hydrogenation, it is preferable to use finely divided cobalt and, particularly, finely divided nickel (Raney cobalt or Raney nickel).

It is not necessary to isolate intermediately the compounds of the formula III. On the other hand, it is advisable to remove the catalysts used in the first stage before a further reaction is carried out, for example by filtration, if necessary using filter aids, such as silica gel.

Tert.-butanol, ethylene glycol monomethyl and monoethyl ethers, n-hexane and cyclohexane should be mentioned as examples of inert organic solvents which are suitable for carrying out the hydrogenation according to the invention.

The hydrogenation reactions are generally carried out in a closed system and - at least in the final stage - under pressure.

Depending on the nature of the compounds of the formula II and/or the catalysts employed, the reaction temperatures can vary within wide imits. In the one-stage process they are generally between 120° and 220° C, preferably between about 140° and 180° C.

In the two-stage hydrogenation the reaction temperatures during the first phase are appropriately between about 20° and 130° C and are subsequently raised to about 170° to 220° C.

After the completion of the reaction the catalysts and the solvent are removed in a customary manner.

The substituted 1,10-diaminodecanes according to the invention are generally obtained as mixtures of diastereomers in the form of colourless oils and can be isolated and purified in a manner which is in itself known.

The starting compounds of the formula II are known or can be manufactured in a manner which is in itself known, by reacting 1,3- butadiene with an azine of the formula

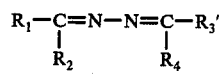

at temperatures of up to 100° C, preferably at 70°-95° C, in the presence of a catalyst which is obtained under reducing conditions by the action of an electron donor on carbon monoxide-free compounds of nickel. It is preferably here to employ catalysts which are obtained by reducing a carbon monoxide-free compound of nickel by means of halogen-free metal alkyls or metal aryls in the presence of electron donors, for example a catalyst which is obtained by reducing nickel acetylacetonate by means of ethoxy-diethyl-aluminium in the presence of triphenylphosphine.

The manufacture of some 1,10-diaminodecanes according to the invention is described in the following examples.

A. PREPARATIVE EXAMPLES

Example 1

(a) 3,12-Dicyclohexyl-1,2-diaza-1,5,9-cyclododecatriene

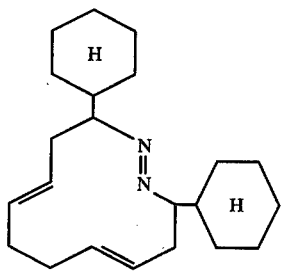

8.8 g (0.034 mol) of nickel acetylacetonate and 8.8 g (0.033 mol) of triphenylphosphine are dissolved in 500 ml of absolute toluene. Approx. 20 g of 1,3-butadiene are introduced into the clear, green solution at room temperature (20°–25° C). Reduction is then carried out at room temperature by means of 14 ml (0.09 mol) of ethoxydiethyl-aluminum, the color of the solution changing from green to orange-red. The mixture is now warmed as quickly as possible to 80° C, while passing in a steady stream of 1,3-butadiene. 991 g (4.5 mols) of cyclohexylaldazine, dissolved in 1.6 l of absolute toluene, are then added dropwise in such a way that, on the one hand the exothermic reaction which now sets in does not rise above 90°–95° C (cooling) and, on the other hand, butadiene is always present in excess in the reaction solution. After a dropwise addition time of 50 minutes, the mixture is subsequently stirred for a further 15 minutes and part of the toluene (approx. 1 l) is then distilled off under a slight waterpump vacuum using a descending condenser.

After cooling to 20°–25° C, 3 l of isopropanol are added and the mixture is cooled to 0° C. A diastereomeric mixture of 3,12-dicyclohexyl-1,2-diaza-1,5,9-cyclododecatriene is precipitated in the form of colourless crystals; these are filtered off, washed with a little cold methanol and then dried over phosphorus pentoxide in a vacuum drying cabinet at room temperature. 973.5 g of reaction product are obtained. The mother liquor is now evaporated and 1.8 l of acetone are added to the resulting green syrup. A further 260 g of 3,12-dicyclohexyl-1,2-diaza-1,5,9-cyclododecatriene are precipitated.

The total yield therefore amounts of 1,233.5 g = 91.1% theory, relative to cyclohexylaldazine employed (mixture of diastereomers); melting point 102°–3° C.

Analysis for $C_{22}H_{36}N_2$ (molecular weight 328.5): Calculated; C, 80.42%; H, 11.04%; N, 8.53% Found: C, 80.44%; H, 10.96%; N, 8.53%.

(b) 1,10-Dicyclohexyl-1,10-diaminodecane

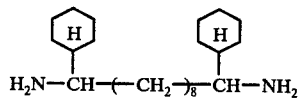

328.5 g (1 mol) of 3,12-dicyclohexyl-1,2-diaza-1,5,9-cyclododecatriene are dissolved in 2.6 l of pure tert.-butanol and the mixture is slowly heated to 180°–200° C in a stirred autoclave (temperature increase approx. 30° C per hour). 33 g of a rhodium-aluminium oxide catalyst (5% by weight of Rh) are added at this temperature and the mixture is hydrogenated for 8 hours (initial pressure 120 bars). At the end of this time the autoclave is cooled to room temperature (20°–25° C). The catalyst is filtered off through kieselguhr and rinsed with 100 ml of tert.-butanol. The solvent is then evaporated in a rotary evaporator at 12 mm Hg. Residual solvent is then removed in a high vacuum at a bath temperature of 60° C. This gives 320 g of a colourless, oily residue. The reaction product is purified via the corresponding bis-hydrochloride, by dissolving the residue in 1.8 l of anhydrous diethyl ether and cooling the resulting solution to 0°–5° C, after which hydrogen chloride is passed in until the ether solution is saturated. A colourless, crystalline precipitate is formed which is filtered off, rinsed with diethyl ether and dried in the air. This precipitate is dissolved in water and the pH of the solution is adjusted to at least 14 by means of concentrated sodium hydroxide solution. The aqueous phase is extracted with diethyl ether and the ethereal solution is washed with water and dried over $MgSO_4$. The diethyl ether is evaporated off in a rotary evaporator and the residue is distilled through a short Vigreux column in a high vacuum. This gives 304 g (0.904 mol) of colourless 1,10-dicyclohexyl-1,10-diaminodecane; boiling point 190°–193° C/0.05 mm Hg; yield: 90.4% of theory, relative to 3,12-dicylohexyl-1,2-diaza-1,5,9-cyclododecatriene reacted; $n_D^{20}$: 1.4944.

Gas chromatogram: Signal at 97.3% and 1.7% (mixture of diastereomers).

Analysis for: $C_{22}H_{44}N_2$ (molecular weight 336.58): Calculated C, 78.45%; H, 13.20%; N, 8.35%; Found C, 78.8%; H, 13.40%; N, 8.2 %.

Mass spectrogram: molecule peak 336; fragment masses 253, 236, 154 and 112.

$H^1$-NMR spectrum (100 Megahertz [MHz]): δ [ppm] = 2.4 (multiplet), 1.7 (multiplet), 1.3 (multiplet), 1.1 (multiplet), 1.0 (singlet) in the ratio of 2:38:4.

For further characterisation, 1.1 g of 1,10-dicyclohexyl-1,10-diaminodecane are boiled under reflux in 4 ml of acetic anhydride for 10 minutes. After cooling the reaction mixture to 20°–25° C, colourless crystals are precipitated which are recrystallised once from ethanol and are dried at 100° C in a high vacuum. This gives 0.85 g of the compound of the formula

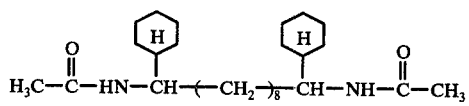

in the form of colourless crystals; melting point 217°–219° C.

Analysis for $C_{26}H_{48}N_2O_2$ (molecular weight 420.68): Calculated; C, 74.24%; H, 11.50%; N, 6.66%; Found C, 74.05%; H, 11.46%; N 6.75%.

Mass Spectrogram: molecule peak 420; fragment masses 41, 337, 295, 236 and 154.

Example 2

(a) 3,12-Dimethyl-1,2-diaza-1,5,9-cyclododecatriene

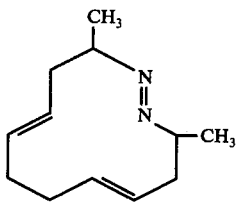

22 g (85 mmols) of nickel acetylacetonate and 22 g (84 mmols) of triphenylphosphine are dissolved in 2 l of absolute toluene. Approx. 40 g (0.74 mol) of 1,3-butadiene are introduced into the green, clear toluene solution at room temperature (20°–25° C). Reduction is then carried out at room temperature by means of 35 ml (220 mmols) of ethoxydiethylaluminium, the colour of the solution changing from green to orange-red. The mixture is now warmed as rapidly as possible to 80° C while passing in a steady stream of 1,3-butadiene; 725 g (8.63 mols) of diethylidene-hydrazine (acetaldazine) are then added dropwise in such a way that a slight excess of 1,3-butadiene is always present. After the first addition of diethylidenehydrazine, the colour of the reaction solution changes to brown and an exothermic reaction sets in; in the course thereof, suitable cooling is applied to ensure that the temperature does not rise above 95° C. After an addition time of 2 hours, the mixture is stirred for a further 1 hour at 90°–92° C while continuing to pass in a moderate stream of 1,3-butadiene. After cooling, the catalyst is deactivated with 100 ml of triphenylphosphite. The toluene and any by-products which may have been formed are distilled off under a slight waterpump vacuum (20–30 mm Hg). The residue is fractionally distilled (40 cm Vigreux column) under a waterpump vacuum. This gives 1,375 g of 3,12-dimethyl-1,2-diaza-1,5,9-cyclododecatriene as a colourless oil; yield: 83% of theory, relative to diethylidenehydrazine reacted (conversion 100%); boiling point 110° C/10 mm Hg; $n_D^{20}$ = 1,4861.

Mass spectrogram: molecule peak 192, fragment masses 177, 82, 67 and 54

$H^1$-NMR spectrum (100 MHz) δ [ppm] = 5 (multiplet), 3.5 – 3.8 (multiplet) 1.5 – 2.8 (multiplet), 1.2 (doublet) in the ratio of 4:2:8:6.

(b) 1,10-Dimethyl-1,10-diaminodecane

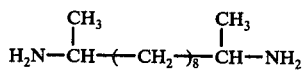

290.8 g (1.52 mols) of 3,12-dimethyl-1,2-diaza-1,5,9-cyclododecatriene are dissolved in 1.8 l of pure tert.-butanol. The reaction solution is then slowly heated to 140°–150° C in a stirred autoclave (temperature increase approx. 30° C per hour), 30 g of rhodium-aluminum oxide catalyst (5% by weight of Rh) are added and hydrogenation is carried out at this temperature for 14 hours (initial pressure 120 bars). After cooling the autoclave to room temperature, the catalyst is filtered off through silica gel and rinsed with 90 ml of tert.-butanol. The solvent is removed, first in a rotary evaporator at 12 mm Hg and then in a high vacuum at a bath temperature of 60° C. This gives 288 g of a colourless, oily residue. This residue is worked up as described in Example 1b) in order to characterise it and purify it. This gives 252 g (1.255 mols) of colourless 1,10-dimethyl-1,10-diaminodecane; boiling point 73° C/0.1 mm Hg; $n_D^{20}$ = 1.4549.

Gas chromatogram: single signal at 98%.

Analysis for $C_{12}H_{28}N_2$ (molecular weight 200.344): Calculated: C, 71.83%; H, 14.09%; N 13.96%; Found: C, 71.75%; H, 14.32%; N, 13.75%.

Mass spectrogram: Molecule peak 200; fragment masses 199, 185, 168, 157, 142 and 44.

$^{13}$-C-NMR spectrum (Shifts in ppm of trimethylsilane; solvent $CDCl_3$)

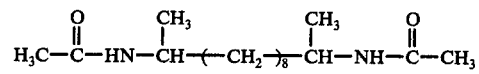

| | |
|---|---|
| 47.0 (doublet) | C-2 |
| 40.2 | C-3 |
| 29.8 ⎫ | |
| 29.6 ⎭ | C-5, C-6 |
| 26.5 | C-4 |
| 24.1 (quartet) | C-1 ($CH_3$) |

For further characterisation, the above 1,10-dimethyl-1,10-diaminodecane is converted, as described in Example 1, into the corresponding bis-acetyl derivative of the formula $$H_3C-\overset{O}{\underset{\|}{C}}-HN-\overset{CH_3}{\underset{|}{CH}}-(CH_2)_8-\overset{CH_3}{\underset{|}{CH}}-NH-\overset{O}{\underset{\|}{C}}-CH_3$$

melting point 119° C.

Analysis for $C_{16}H_{32}N_2O_2$ (molecular weight 284.446): Calculated: C, 67.55%; H, 11.36%; N, 9.84%; Found: C, 67.9%; H, 11.5%; N, 9.8%.

EXAMPLE 3

(a) 3,12-Diisopropyl-1,2-diaza-1,5,9-cyclododecatriene

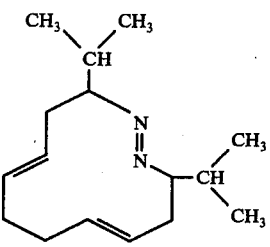

If 232 g (2.4 mols) of bis-(2-methylpropylidene)hydrazine (isobutyraldazine) are used in Example 2 a) instead of 725 g (8.63 mols) of diethylidenehydrazine, an otherwise identical procedure gives, after a refining distillation at 0.03 mm Hg, 426 g of 3,12-diisopropyl-1,2-diaza-1,5,9-cyclododecatriene as a colourless oil; boiling point 89°–92° C/0.03 mm Hg; yield 72% of theory relative to bis-(2-methylpropylidene)-hydrazine reacted (100% conversion).

Mass spectrogram: molecule peak 248, fragment masses 205, 110 and 95.

Analysis for $C_{16}H_{28}N_2$ (molecular weight 248.41): Calculated: C, 77.36%; H, 11.36%; N 11.28%; Found: C, 77.26%; H, 11.57%; N, 11.24%.

(b) 1,10-Diisopropyl-1,10-diaminodecane

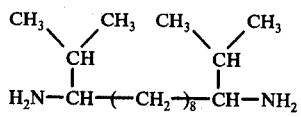

250 g (1 mol) of 3,12-diisopropyl-1,2-diaza-1,5,9-cyclododecatriene are dissolved in 1.5 l of pure tert.-butanol in a stirred autoclave. The reaction solution is slowly heated to 140°-150° C, 25 g of a rhodium-aluminium oxide catalyst (5% by weight of Rh) are added and hydrogenation is carried out at this temperature for 14 hours (initial pressure 120 bars).

After cooling the autoclave to 20°-25° C, the catalyst is filtered off through kieselguhr and rinsed with 130 ml of tert.-butanol. The solvent is removed, first in a rotary evaporator at 12 mm Hg and subsequently in a high vacuum at a bath temperature of 60° C. This gives 264 g of a colourless, oily residue.

High-vacuum distillation of this residue through a short Vigreux column gives 8 g of fore-runnings followed by 238 g (0.92 mol) of colourless 1,10-diisopropyl-1,10-diaminodecane; boiling point 106°-109° C/0.01 mm Hg; $n_D^{20} = 1.4600$.

Yield: 92% of theory, relative to 3,12-diisopropyl-1,2-diaza-1,5,9-cyclododecatriene reacted.

Gas chromatogram: signal at 96.8% and 2% (mixture of diastereomers).

Analysis for $C_{16}H_{36}N_2$ (molecular weight 256.47): Calculated: C, 74.92%; H, 14.15%; N, 10.92%; Found: C, 74.77%; H; 14.34%; N, 10.71%.

Mass spectrogram: molecule peak 256; fragment masses 238, 213, 196, 142, 123, 109, 97, 83, 72, 56 and 44.

$H^1$-NMR spectrum (100 Megahertz): δ[ppm] = 0.84 (doublet), 0.88 (doublet), 0.99 (singlet), 1.29 (singlet), 1.56 (multiplet) and 2.48 (multiplet) in the ratio of 6:6:4:16:2:2.

EXAMPLE 4

(a) 3,3,12,12-Tetramethyl-1,2-diaza-1,5,9-cyclododecatriene

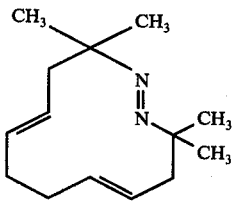

If 602 g (5.37 mols) of acetone-azine are used in Example 2 (a) instead of 725 g (8.63 mols) of diethylidenehydrazine, an otherwise identical procedure gives, after the refining distillation at 0.02 mm Hg, 1,103 g of 3,3,12,12-tetramethyl-1,2-diaza-1,5,9-cyclododecatriene (boiling point 63°-5° C/0.02 mm Hg) as a colourless oil; yield 93.2% of theory, relative to acetone-azine reacted (100% conversion).

Mass spectrogram: molecule peak 220; fragment masses 205, 192, 96 and 81.

$H^1$-NMR spectrum (100 MHz): δ[ppm] = 4.95 (multiplet), 2.35 - 2.50 (multiplet), 1.90 - 2.10 (multiplet) and 1.15 (singlet) in the ratio of 4:4:4:12.

(b) 1,1,10,10-Tetramethyl-1,10-diaminodecane

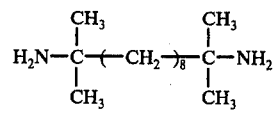

660 g (3 mols) of 3,3,12,12-tetramethyl-1,2-diaza-1,5,9-cyclododecatriene are dissolved in 4 l of anhydrous (pure) ethylene glycol monomethyl ether in a stirred autoclave and are hydrogenated, with the addition of 30 g of palladium-on-charcoal catalyst (5% by weight of Pd), first at 20°-25° C for 30 minutes and then at 110°-120° C for 8 hours. After the autoclave has been cooled to room temperature, the catalyst is filtered off through silica gel and rinsed with 100 ml of ethylene glycol monomethyl ether.

200 ml of cold water are added to the resulting clear reaction solution, whereupon the 3,3,12,12-tetramethyl-1,2-diazacyclododecane of the formula

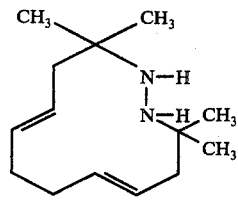

is precipitated in the form of colourless crystals. This product is filtered off, washed twice with a little cold methanol and then dried for 6 hours over $P_2O_5$ in a high vacuum; melting point 50°-54° C.

Yield: 617 g = 91% of theory, relative to 3,3,12,12-tetramethyl-1,2-diaza-1,5,9-cyclododecatriene reacted.

Analysis for $C_{14}H_{30}N_2$ (molecular weight 226.4): Calculated: C, 74.24%; H, 13.36%; N, 12.38%; Found: C, 74.10%, H, 13.39%; N, 12.50%.

Mass spectrogram: molecule peak 226; fragment masses 211, 113, 73 and 55.

565 g (2.5 mols) of the above 3,3,12,12-tetramethyl-1,2-diazacyclododecane are dissolved in 2.8 l of pure tert.-butanol and are treated, in a stirred autoclave, with 380 g of ammonia and 110 g of Raney nickel. The reaction mixture is slowly heated to 230° C (initial pressure 120 bars) and is hydrogenated at this temperature for 16 hours.

The autoclave is then cooled to 20°-25° C and the catalyst is filtered off through silica gel and rinsed with 130 ml of tert.-butanol. The solvent is removed, first in a rotary evaporator at 12 mm Hg and then in a high vacuum at a bath temperature of 60° C. This gives 555 g of a colourless, oily residue. Subsequent high-vacuum distillation of this residue gives 78 g of fore-runnings, consisting of 2,11-dimethyldodecane; boiling oint 76°-80° C/0.01 mm Hg; mass spectrum: molecule peak 198, fragment masses at 183, 155, 57 and 43, and, as the main fraction, 452 g of 1,1,10,10-tetramethyl-1,10-diaminodecane; boiling point 93° C/0.01 mm Hg; $n_D^{20} = 1.453$. Yield:81% of theory, relative to 3,3,12,12-tetramethyl-1,2-diazacyclododecane reacted.

Gas chromatogram: signal at 98.2% and 1.2% (mixture of diastereomers).

If the purification of the end product is carried out via the bis-hydrochloride as indicated in Example 1(b), a product is obtained which is 99% pure according to gas chromatography.

Analysis for $C_{14}H_{32}N_2$ (molecular weight 228.41): Calculated: C, 73,58%; H, 14.12%; N, 12.25%; Found: C, 73.24%; H, 14.28%; N, 12.06%.

Mass spectrogram: molecule peak (M+1) 229; fragment masses: 213, 196 and 58.

$H^1$-NMR spectrum: (100 MHz) + $D_2O$. δ [ppm] = 1.07 (multiplet) and 1.29 (singlet) in the ratio 12:16.

For further characterisation, the above 1,1,10,10-tetramethyl-1,10-diaminodecane is converted as described in Example 1 into the corresponding bis-acetyl derivative of the formula

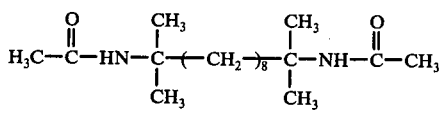

melting point 147°–148° C.

Analysis for $C_{18}H_{36}N_2O_2$ (molecular weight 312.478): Calculated: C, 69.20%; H, 11.61%; N, 8.96%; Found: C, 69.30%; H, 11.67%; N, 8.92%.

$H^1$-NMR spectrum (100 MHz): δ [ppm] = 5.5 (multiplet), 1.90 (singlet), 1.29 (singlet) and 1.6 (multiplet) in the ratio of 2:6:28:4.

EXAMPLE 5

(a) 3,12-Diethyl-3,12-dimethyl-1,2-diaza-1,5,9-cyclododecatriene

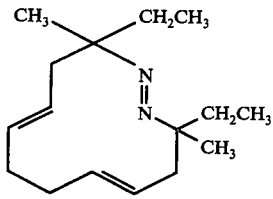

2.56 g (10 mmols) of nickel acetylacetonate and 2.6 g (10 mmols) of triphenylphosphine are dissolved in 50 ml of absolute toluene and the solution is saturated with butadiene at room temperature. Reduction is then carried out at room temperature using 3.9 ml (25 mmols) of ethoxydiethyl-aluminum, the catalyst solution thus obtained is warmed to 85°–95° C while passing in butadiene continuously and 173 g (1.24 mols) of 2-butylidenehydrazine (2-butanone-azine) are added dropwise at this temperature in such a way that there is always a slight excess of butadiene. After an addition time of 30 minutes, stirring is continued for a further 30 minutes at 90° C, the reaction solution is allowed to cool and the catalyst is deactivated by adding 0.5–1 g of sulfur.

The toluene and any volatile by-products which may have been formed and stripped off under a waterpump vacuum and the residue is fractionated at 0.4 mm Hg. This gives 167 g (55%) of 3,12-diethyl-3,12-dimethyl-1,2-diaza-1,5,9-cyclododecatriene (mixture of diastereomers) as a colourless oil, boiling point 103°–4° C/0.4 mm Hg; $n_D^{20}$ = 1.4895.

Analysis: $C_{16}H_{28}N_2$ (248.41); Calculated: C, 77.36; H, 11.36; N, 11.28; Found: C, 77.63; H, 11.54; N, 11.16;

100 MHz Proton magnetic resonance spectrum ($CDCl_3$): δ[ppm] 0.8 (f); 1.0 (s); 1.1 (s); 1.4–2.8 (m) and 4.8–5.1 (m) in the ratio of 6:3:3:12:4.

(b) 1,10-Diethyl-1,10-dimethyl-1,10-diaminodecane 124 g (0.5 mol) of 3,12-diethyl-3,12-dimethyl-1,2-diaza-1,5,9-cyclododecatriene are hydrogenated, in 620 ml of cyclohexane in a stirred autoclave and with the addition of 12 g of palladium-on-charcoal catalyst (5% by weight of Pd), first at room temperature for 90 minutes and then at 100°–110° C for 60 minutes. After filtering off the catalyst and stripping off the solvent on a rotary evaporator, 123 g (97%) of 3,12-diethyl-3,12-dimethyl-1,2-diazacyclododecane (mixture of diastereomers) are produced as a yellowish oil.

23 g (90 mmols) of the above 3,12-diethyl-3,12-dimethyl-1,2-diazacyclododecane are hydrogenated, in 200 ml of cyclohexane in a stirred autoclave and with the addition of 3 g of rhodium-aluminum oxide catalyst (5% by weight of Rh), for 17 hours at 200° C. After filtering off the catalyst and stripping off the solvent on a rotary evaporator, the residue is fractionated at 0.2 mm Hg. This gives 7.7 g (30%) of 1,10-diethyl-1,10-dimethyl-1,10-diaminodecane as a colorless oil, boiling point 118°–22° C/0.2 mm Hg, $n_D^{20}$ = 1.4597.

Analysis $C_{16}H_{36}N_2$ (256.48); Calculated: C, 74.93; H, 14.15; N, 10.92; Found: C, 75.08; H, 14.18; N, 11.00.

100 MHz Proton magnetic resonance spectrum ($C_6O_6$); δ[ppm] 0.66 (s); 0.84 (f); 0.94 (s) and 1.1–1.5 (m) in the ratio of 4:6:6:20.

EXAMPLE 6

(a) 3,12-Dicyclooctyl-1,2-diaza-1,5,9-cyclododecatriene

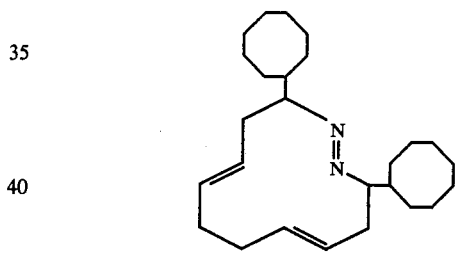

1.25 g (5 mmols) of nickel acetylacetonate and 1.25 g (5 mmols) of triphenylphosphine are dissolved in 75 ml of absolute toluene in an ampoule and 20 g of butadiene are co-condensed. Reduction is then carried out at room temperature using 1.8 ml (12 mmols) of ethoxydiethyl-aluminum, 13.8 g (50 mmols) of cyclooctylcarbaldazine are added to the catalyst solution obtained in this way and the mixture is stirred for 62 hours at room temperature. The catalyst is then deactivated, the reaction solution is diluted with 200 ml of toluene and filtered through silica gel and the solvent is stripped off on a rotary evaporator. Crystallisation of the residue from ethanol gives 6.3 g (33% of 3,12-dicyclooctyl-1,2-diaza-1,5,9-cyclododecatriene. Melting point 62°–63° C.

Analysis: $C_{26}H_{44}N_2$ (384.65): Calculated: C, 81.19; H, 11.53; N, 7.28; Found: C, 81.30; H, 11.59; N, 7.48.

100 MHz Proton magnetic resonance spectrum ($CDCl_3$) δ[ppm] 1.1–2.9 (multiplet); 3.03 (doublets)1 3.14 (doublets); 4.8–5.1 (multiplet) in the ratio of 38:1:1:4.

(b) 1,10-Dicyclooctyl-1,10-diaminodecane 2.5 g (6.5 mmols) of 3,12-dicyclooctyl-1,2-diaza-1,5,9-cyclododecatriene are hydrogenated, in 100 ml of cyclohexane in a stirred autoclave and with the addition of 0.6 g of rhodium-aluminum oxide (5% by weight of rhodium), first at room temperature for 90 minutes and then at 210°-220° C for 6 hours. After filtering off the catalyst and stripping off the solvent on a rotary evaporator, 2.4 g of crude 1,10-dicyclooctyl-1,10-diaminodecane are produced.

For isolation and characteristics, the above diamine is converted into the corresponding bis-acetyl derivative and the latter is recrystallised from ether/acetonitrile. This gives 0.85 g (27%) of N,N'-bisacetyl-(1,10-dicyclooctyl-1,10-diaminodecane), melting point 144°-9° C.

Analysis $C_{30}H_{56}N_2O_2$ (476.79): Calculated C, 75.57; H, 11.84; N, 5.87; O, 6.71; Found: C, 75.34; H, 12.03; N, 5.84; O, 7.09.

100 MHz Proton magnetic resonance spectrum $(CDCl_3)$: δ[ppm] 1.0–1.8 (multiplet); 1.98 (singlet); 3.76 (multiplet); and 5.6 (doublet) in the ratio of 46:6:2:2.

EXAMPLE 7

(a) 3,12-Diheptyl-1,2-diaza-1,5,9-cyclododecatriene

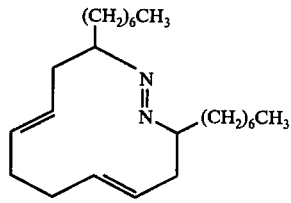

If 37.9 g (0.15 mol) of caprylaldazine are used in Example 5 (a) instead of 173 g (1.24 mols) of 2-butylidenehydrazine under otherwise identical reaction conditions and if the mixture is worked up as in Example 6a, 8.9 g (16%) of 3,12-diheptyl-1,2-diaza-1,5,9-cyclododecatriene are obtained, melting oint 60°-61° C.

Analysis $C_{24}H_{44}N_2$ (360.63): Calculated: C, 79.93; H, 12.30; N, 7.77; Found: C, 79.95; H, 12.56; N, 8.09.

100 MHz Proton magnetic resonance spectrum $(CDCl_3)$: δ[ppm] 0.84 (triplet); 1.23 (multiplet); 1.5–2.0 (multiplet); 2.0–2.9 (multiplet); 3.28 (multiplet) and 5.0 (multiplet) in the ratio of 6:20:8:4:2:4.

(b) 2,10-Diheptyl-2,10-diaminodecane

If 3.6 g (10 mmols) of 3,12-diheptyl-1,2-diaza-1,5,9-cyclododecatriene are used in Example 6b instead of 2.5 g (6.5 mmols) of 3,12-dicyclooctyl-1,2-diaza-1,5,9-cyclododecatriene under otherwise identical reaction conditions, working up in an analogous manner gives 3.5 g of crude 2,10-diheptyl-2,10-diaminodecane as a colourless oil.

For isolation and characterisation, the above diamine is converted into the corresponding bis-acetyl derivative and the latter is recrystallized from n-propanol. This gives 1.4 g (31%) of N,N'-bisacetyl-(1,10-diheptyl-1,10-diaminodecane), melting point 158°-62° C.

Analysis $C_{28}H_{56}N_2O_2$ (452.77): Calculated: C, 74.28; H, 12.47; N, 6.19; O, 7.07; Found: C, 74.29; H, 12.39; N, 6.53; O, 7.29.

The 1,10-diaminodecanes of the formula I are valuable curing agents for epoxide resins. Products and materials cured by means of them are distinguished by good thermal and dielectric properties, but, above all, by improved mechanical properties, such as good impact resistance and high shear strength under tension as well as good adhesion.

Curable mixtures according to the invention which contain a polyepoxide and, as the curing agent, at least one compound of the formula I, are suitable, in particular, for the manufacture of mouldings, impregnated materials, coatings, lacquers and sealings.

It is appropriate to use 0.5 to 1.3 equivalents, preferably approx. 1.0 equivalent, of active hydrogen atoms, linked to nitrogen, of the particular 1,10-diaminodecane of the formula I, per 1 equivalent of epoxide groups of the polyepoxide (a).

Polyepoxides (a) which can be used are above all those which have, on average, more than one glycidyl group, β-methylglycidyl group or 2,3-epoxycyclopentyl group linked to a hetero atom (for example sulfur, but preferably oxygen or nitrogen); special mention should be made of bis-(2,3-epoxycyclopentyl) ether; diglycidyl or polyglycidyl ethers of polyhydric aliphatic alcohols, such as 1,4-butanediol, or polyalkylene glycols, such as polypropylene glycols; diglycidyl or polyglycidyl ethers of cycloaliphatic polyols, such as 2,2-bis-(4-hydroxycyclohexyl)-propane; diglycidyl or polyglycidy ethers of polyhydric phenols, such as resorcinol, bis-(p-hydroxyphenyl)-methane, 2,2-bis-(p-hydroxyphenyl)-propane (= Diomethan), 2,2-bis-(4'-hydroxy-3',5'-dibromophenyl)-propane or 1,1,2,2-tetrakis-(p-hydroxyphenyl)-ethane, or of condensation products of phenols and formaldehyde which are obtained under acid conditions, such as phenol novolacs and cresol novolacs; di- or poly-(β-methylglycidyl) ethers of the abovementioned polyhydric alcohols or polyhydric phenols; polyglycidyl esters of polybasic carboxylic acids, such as phthalic acid, terephthalic acid, $\Delta^4$-tetrahydrophthalic acid and hexahydrophthalic acid; N-glycidyl derivatives of amines, amides and heterocyclic nitrogen bases, such as N,N-diglycidyl aniline, N,N-diglycidyltoluidine and N,N,N',N'-tetraglycidyl-bis-(p-aminophenyl)-methane; triglycidyl isocyanurate; N,N'-diglycidyl ethyleneurea; N,N'-diglycidyl-5,5-dimethylhydantoin, N,N'-diglycidyl-5-isopropylhydantoin and N,N'-diglycidyl-5,5-dimethyl-6-isopropyl-5,6-dihydrouracil.

If desired, the viscosity of the polyepoxides can be reduced by adding active diluents, such as styrene oxide, butyl glycidyl ether, isooctyl glycidyl ether, phenyl glycidyl ether, cresyl glycidyl ether and glycidyl esters of synthetic, highly branched aliphatic monocarboxylic acids which are mainly tertiary.

The curable mixtures according to the invention are appropriately cured to give moulded articles and the like within the temperature range from 20° to 160° C. The curing can also be carried out in a known manner in two or more stages, the first curing stage being carried out at a lower temperature and the post-curing at a higher temperature.

If desired, the curing can also be carried out in 2 stages in such a way that the curing reaction is first discontinued prematurely or the first stage is carried out at room temperature (20°-25° C) or at an only slightly elevated temperature, a curable procondensate which is still fusible and/or soluble (so-called "B stage") being obtained from the epoxide component (a) and the curing agent (b). A precondensate of this kind can be used, for example, for the manufacture of "prepregs", compression moulding compositions or, in particular, sintering powders.

In order to shorten the gelling or curing times, it is possible to add accelerators which are known for amine curing, for example monphenols or polyphenols, such as phenol or Diomethan, salicylic acid, tertiary amines or salts of thiocyanic acid, such as $NH_4SCN$.

The expression "cure", as used here, denotes the conversion of the soluble, either liquid or fusible polyepoxides into solid, insoluble and infusible products or materials which are crosslinked in three dimensions, and, as a rule, with simultaneous shaping to form shaped articles, such as cast articles, moulded articles and laminates, and to form impregnated materials, coatings, lacquer films or sealings.

The curable mixtures according to the invention formed from polyepoxides (a) and 1,10-diaminodecanes of the formula I as the curing agent can also be treated, before curing, in any phase with customary modifying agents, such as extenders, fillers and reinforcing agents, pigments, dyestuffs, organic solvents, plasticisers, flow control agents, thixotropic agents, flame-retarding materials and mould release agents.

The following examples should be mentioned as extenders, reinforcing agents, fillers and pigments which can be employed in the curable mixtures according to the invention: coal tar, bitumen, textile fibers, glass fibers, asbestos fibers, boron fibers, carbon fibers, cellulose, polyethylene powder and polypropylene powder; quartz powder, mineral silicates, such as mica, ground asbestos and ground shale; kaolin, aluminum oxide trihydrate, ground chalk, gypsum, antimony trioxide, bentonite, silicic acid aerogel, lithopone, barite, titanium dioxide, carbon black, graphite, oxide colorants, such as iron oxide, or metal powders, such as aluminum powder or iron powder.

Examples of organic solvents which are suitable for modifying the curable mixtures are toluene, xylene, n-propanol, butyl acetate, acetone, methyl ethyl ketone, diacetone alcohol and ethylene glycol monomethyl, monoethyl and monobutyl ethers.

Examples of plasticizers which can be employed for modifying the curable mixtures are dibutyl, dioctyl and dinonyl phthalates, tricresyl phosphate, trixylenyl phosphate and also polypropylene glycols.

Examples of flow control agents which can be added when using the curable mixtures, particularly in protecting surfaces, are silicones, cellulose acetobutyrate, polyvinylbutyral, waxes, stearates and the like (which can, in part, also be used as mould release agents).

Especially when used in the field of lacquers, it is also possible for the polyepoxides to be partially esterified in a known manner with carboxylic acids, such as, in particular, higher unsaturated fatty acids. It is also possible to add other curable synthetic resins, for example phenoplasts or aminoplasts, to such lacquer resin formulations.

The production of the curable mixtures according to the invention can be carried out in a customary manner with the aid of known mixing units (stirrers, kneaders, rollers and the like).

The curable epoxide resin mixtures according to the invention are employed above all in the fields of surface protection, the electrical industry, laminating processes and in the building industry. They can be used in a formulation which is suited in each particular case to the special end use, in an unfilled or filled state, if appropriate in the form of solutions or emulsions, as paints or lacquers, as sintering powders. compression moulding compositions, injection moulding formulations, dipping resins, casting resins, impregnating resins, binders and adhesives, and as moulding resins, laminating resins, sealing compositions and primers, flooring compositions and binders for mineral aggregates.

The epoxide resin which follows was used for the production of curable mixtures, which is described in the following use examples:

Epoxide resin A

A polyglycidyl ether resin (an industrial product) which is manufactured by condensation of 2,2-bis-(p-hydroxypheyl)-propane with a stoichiometric excess of epichlorohydrin in the presence of alkali, and which mainly consists of Diomethan diglycidyl ether of the formula

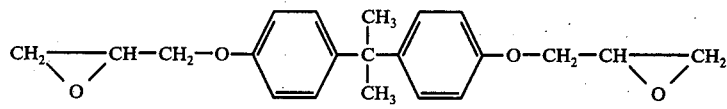

and which is liquid at room temperature and has the following characteristics:
Epoxide content: 5.1 – 5.5 epoxide equivalents/kg
Viscosity (Hoeppler) at 25° C: 9000 – 13,000 cP.

B. Use Examples

The following curable mixtures are used:
Example I: 100 g of epoxide resin A and 44.5 g of 1,10-dicyclohexyl-1,10-diaminodecane prepared in accordance with Example 1.

Example II: 100 g of epoxide resin A and 26.5 g of 1,10-dimethyl-1,10-diaminodecane prepared in accordance with Example 2.

Example III: 100 g of epoxide resin A and 30.2 g of 1,1,10,10-tetramethyl-1,10-diaminodecane prepared in accordance with Example 4.

Comparison Examples

Example IV: 100 g of epoxide resin A and 12.8 g of triethylenetetramine.

Example V: 100 g of epoxide resin A and 31.5 g of 4,4'-methylene-bis-(3-methylcyclohexylamine)[3,3'-dimethyl-4,4'-diamino-dicyclohexylmethane].

Examle VI: 100 g of epoxide resin A and 22.5 g of 3-aminomethyl-3,5,5-trimethylcyclohexylamine.

Example VII: 100 g of epoxide resin A and 21 g of trimethylhexamethylenediamine.

The test specimens are prepared by mixing the diamines with the epoxide resin at room temperature (20°–25° C), briefly degassing the mixture in vacuo and then casting it as indicated below to form sheets or films. Curing is carried out first for 24 hours at 40° C and then for 6 hours at 100° C.

3 mm thick sheets are prepared from the above mixtures in an aluminium mould in order to determine the mechanical properties, that is to say the flexural strength, the bending angle and the impact flexural strength according to Dynstat (compare W. Holzmüller and K. Altenburg, "Physik der Kunststoffe", Akademie-Verlag Berlin, 1961, pages 597–604) and the increase in weight after storage in water.

Sheets 2 mm thick are prepared from the above mixtures in an aluminium mould in order to determine the electrical properties, that is to say the dielectric loss factor tan δ according to DIN 53,483 (= ASTM D 150), the dielectric constant ε according to DIN 53,483 and the specific volume resistivity according to DIN 53,482.

Small sheets 1.5 mm thick are cast from the above mixtures on an aluminium mould in order to determine the glass transition temperature on a differential thermoanalysis apparatus (type TA 2000 of Messrs. Mettler, Greifensee, Switzerland).

Films of 50 μ thickness are produced with the above mixtures by means of a drawing triangle on iron sheets degreased with trichloromethylene and the impact deep-drawing value, after being struck from behind with a hammer, and the Erichsen deepdrawing values (DIN 53,156) are measured on these films.

Test strips of Anticorodal B (an aluminium alloy containing magnesium and silicon of Messrs. Schweizer Aluminium AG; 170 × 25 × 1.5 mm) which have been roughened by grinding and cleansed by washing with acetone are coated at their ends with the above mixtures. The coated ends of two test strips are in each case placed upon one another in such a way that they overlap by 10 mm and are then fixed in this position by a clamp and are cured. The shear strength under tension of the sealing is measured in accordance with DIN 53,283 on the test specimens thus obtained.

The results are summarised in Table I which follows:

gel time and operating time and by means of differential thermo-analysis. The viscosity values also show that the curable mixtures containing the amines according to the invention have a low (that is to say favourable) viscosity.

Differential thermo-analysis

~20 mg of the resin:curing agent mixture to be tested are weighed into a small Al crucible and the crucible is closed and placed on the measuring sensor in the oven of a differential thermo-analyser (type TA 2000 of Messrs. Mettler, Griefensee, Switzerland). The sample is warmed at a heating rate of 4° C/minute and the reaction is followed by measuring the temperature difference between a full and an empty crucible. The temperature at the start of the reaction, the temperature at the maximum reaction rate and the temperature at the end of the reaction are read off from the curve which is produced and the heat liberated during the reaction is determined by measuring the area below the curve.

Measurement of operating time

The change in viscosity with time is determined under isothermal conditions in a Hoeppler falling ball viscosimeter at 25° and at 40° C on another portion of the resin-curing agent mixture and the time required to reach 1,500, 3,000 and 10,000 cP is recorded.

TABLE I

| Properties | Cast specimen according to | | | | |
|---|---|---|---|---|---|
| | Example I | Example II | Example III | Comparison Example IV | Comparison Example V |
| Impact flexural strength according to Dynstat (cm.kg/cm$^2$) | 21.0 | 16.5 | 27.0 | 8.3 | 13.0 |
| Flexural strength according to Dynstat (kg/mm$^2$) | 1225 | 1195 | 1175 | 1335 | 1450 |
| Bending angle according to Dynstat (° C) | 53 | 52 | 56 | 49 | 55 |
| Glass transition temperature (° C) | 110 | 97 | 89 | 113 | 130 |
| Water pick-up after storing for 4 days in water at 25° C (%) | 0.20 | 0.29 | 0.20 | 0.26 | 0.35 |
| Water pick-up after storing for 1 hour in boiling water (%) | 0.30 | 0.61 | 0.40 | 0.45 | 0.36 |
| Shear strength under tension on Anticorodal B according to DIN 53,283 (kg/mm$^2$) | 0.9 | 1.8 | 1.5 | 0.4 | — |
| Appearance of the lacquer film | High gloss | Matt | High gloss | Slightly cloudy | |
| Erichsen deep-drawing value according to DIN 53,156 (mm at 20° C) | 7.3 | 9.3 | 7.6 | 4.9 | 5.4 |
| Impact deep-drawing value, struck from behind (cm/kg hammer) | 40/1 | 90/2 | 80/2 | 30/1 | 25/1 |
| Dielectric loss factor according to DIN 53,483 tan δ > 1% above | 98° | 94° | 75° | 73° | 120° |
| > 5% above | 132° | 108° | 90° | 98° | 165° |
| Dielectric constant ε at 25° C | 3.9 | 4.1 | 3.9 | 4.6 | 5.0 |
| Specific volume resistivity at 25° C (ohm . CM) | $6.4 \times 10^{16}$ | $4.4 \times 10^{16}$ | $2.4 \times 10^{16}$ | $5 \times 10^{16}$ | $5 \times 10^{16}$ |
| DIN = German Industrial Standards | | | | | |

The reactivity of the 1,10-diaminodecanes according to the invention as curing agents for epoxide resins is, surprisingly, much lower than would be expected by virtue of the aliphatic character in itself. These new curing agents therefore represent a technical advance. The difference in reactivity compared with conventional aliphatic amines is illustrated by measuring the Measurement of gel time Finally, the gel time is determined on another sample of the resin-curing agent mixture at 80°, 100° and 120° C on a thermostatically-controlled hotplate.

The values obtained are summarised in Table Ia.

Table Ia

| Example | I | II | III | IV | V | VI | VII |
|---|---|---|---|---|---|---|---|
| Initial viscosity at 25° C (cP) | | 525 | | 2,500 | 2,200 | 3,400 | 800 |
| Operating time at 25° C | | | | | | | |
| up to 1,000 cP [minutes] | — | 139 | — | — | — | — | 26 |
| up to 3,000 cP | — | 269 | — | 5 | — | — | 53 |
| up to 10,000 cP | — | 303 | — | 40 | 120 | 60 | 90 |
| Operating time at 40° C | | | | | | | |
| up to 1,500 cP [minutes] | — | 91 | — | 12 | 48 | 24 | 25 |
| up to 3,000 cP | — | 108 | — | 18 | 60 | 33 | 30 |
| up to 10,000 cP | — | 139 | — | 30 | 150 | 42 | 40 |

Table Ia-continued

| Example | | I | II | III | IV | V | VI | VII |
|---|---|---|---|---|---|---|---|---|
| Gel time at | 80° C | — | 30' | — | 7'40" | 27' | 12' | 11'30" |
| | 100° C | — | 10'50" | — | 2'20" | 13'15" | 8'50" | 4'30" |
| | 120° C | — | 5' | — | 1'10" | 6'30" | 4'30" | 1' |
| Path of curve in differential thermo-analysis | Start of reaction (° C) | 48 | 36 | 49 | 32 | 37 | 35 | 33 |
| | Maximum of reaction (° C) | 118 | 104 | 117 | 81 | 105 | 93 | 90 |
| | End of reaction (° C) | 248 | 195 | 245 | 162 | 199 | 197 | 206 |
| | Enthalpy Cal/equivalent | 21,670 | 24,345 | 20,145 | 22,580 | 21,960 | 21,440 | 24,200 |

Films 50μ thick are prepared as described above on degreased iron sheets using the curable mixture II, the following curing conditions being used:
1 day at 20° C,
1 week at 20° C,
1 month at 20° C,
2 months at 20° C and
2 months at 60° C.

The following investigations relating to lacquer technology are then carried out.

Gel time using Tecam apparatus, 100 cm³ in Al can, 20° C Time until dry to permit handling and complete curing time using Landolt apparatus, Δ 200 μm 65% relative humidity Flow, transparency, surface aspect and exudation, visual assessment Hardness by Persoz method, Δ 200 μm, 20° C 65% relative humidity Erichsen deep-drawing value, Δ 200 μm, 20° C, 65% relative humidity, DIN 58,156

Impact test, Δ200 μm, 20° C 65% relative humidity, impact on coating

Mandrel bending test, Δ 200 μm, 20° C 65% relative humidity

Boiling water test, application by brush to sandblasted steel sheet, visual assessment, curing for 10 days at room temperature.

Adhesion, application by brush to sandblasted steel sheet, visual assessment, curing for 10 days at room temperature.

The results are summarised in Table II which follows:

Table II

| Test | Test value |
|---|---|
| Gel time hours | 9½ |
| Time until dry to permit handling (hours) | 15 |
| Complete curing time hours | 18 |
| Exudation | None |
| Hardness by Persoz method | |
| 1 day 20° C seconds | 100 |
| 1 week 20° C seconds | 200 |
| 1 month 20° C seconds | 200 |
| Erichsen test DIN 53,156 | |
| 2 months 20° C μm | 0.5 |
| 2 months 60° C μm | 1-3 |
| Impact test | |
| 2 months 20° C cm.kg | 10 |
| 2 months 60° C cm.kg | 40 |
| Mandrel bending test, 15 mm mandrel | |
| 2 months 20° C | 10° (angle) |
| 2 months 60° C | 60° (angle) |

What we claim is:

1. Curable mixtures which are suitable for the manufacture of mouldings, impregnated materials, coatings, lacquers and sealings, characterised in that they contain (a) a compound having more than one epoxy group and (b), as the curing agent, at least one 1,10-diaminodecane of the formula I

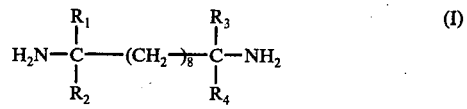

wherein $R_1$ and $R_3$ independently of one another represent an alkyl, cycloalkyl, aralkyl, phenyl or naphthyl group and $R_2$ and $R_4$ independently of one another represent hydrogen, alkyl, cycloalkyl, aralkyl, phenyl or naphthyl group or $R_1$ and $R_2$ and/or $R_3$ and $R_4$, conjointly with the carbon atom to which they are linked, form a 5-membered to 12-membered alkylene or oxaalkylene ring.

2. Mixtures according to claim 1, characterised in that they contain 0.5 to 1.3, preferably approx. 1.0, equivalent of active hydrogen atoms, linked to nitrogen, of the particular 1,10-diaminodecane (b), per 1 equivalent of epoxide groups of the polyepoxide (a).

3. Mixtures according to claim 1, characterised in that they contain, as the curing agent (b), at least one 1,10-diaminodecane of the formula I wherein $R_1$ and $R_3$ independently of one another denote an unsubstituted alkyl group having 1-18, particularly 1-8, carbon atoms, a 1-nuclear or 2-nuclear cycloalkyl group having 5-10 ring carbon atoms, which can be substituted by alkoxy, alkylamino or N,N-dialkylamino groups having in each case 1 or 2 carbon atoms in the alkoxy or alkyl portions, the benzyl or 2-phenylethyl group, an unsubstituted phenyl group or a phenyl group which is substituted by alkyl, alkoxy, alkylamino or N,N-dialkylamino groups having in each case 1 or 2 carbon atoms in the alkyl or alkoxy portions, or an unsubstituted naphthyl group, and $R_2$ and $R_4$ independently of one another denote hydrogen or a group corresponding to $R_1$ or $R_3$.

4. Mixtures according to claim 1, characterised in that they contain, as the curing agent (b), at least one 1,10-diaminodecane of the formula I wherein $R_1$ and $R_2$ and/or $R_3$ and $R_4$, conjointly with the carbon atom to which they are linked form an unsubstituted 5-membered to 12-membered alkylene ring or an unsubstituted 5-membered or 6-membered oxaalkylene ring.

5. Mixtures according to claim 1, characterised in that they contain, as the curing agent (b), at least one 1,10-diaminodecane of the formula I wherein $R_1$ and $R_3$ as well as $R_2$ and $R_4$ have, in each relevant case, the same meaning.

6. Mixtures according to claim 1, characterised in that they contain, as the curing agent (b), at least one 1,10-diaminodecane of the formula I, wherein $R_1$ and $R_3$ each represent an unsubstituted alkyl group having 1-8 carbon atoms or a 1-nuclear or 2-nuclear cycloalkyl group which has 5-10 ring carbon atoms and is unsubstituted or substituted by alkoxy, alkylamino or N,N-dialkylamino groups having in each case 1 or 2 carbon atoms in the alkoxy or alkyl portions, and $R_2$ and $R_4$ each represent hydrogen or an unsubstituted alkyl group having 1-8 carbon atoms.

7. Mixtures according to claim 6, characterised in that they contain, as the curing agent (b), at least one 1,10-diaminodecane of the formula I wherein $R_1$ and $R_3$ are identical and represent an unsubstituted alkyl group having 1 to 8 carbon atoms or a 1-nuclear cycloalkyl group having 6 to 8 ring carbon atoms, and wherein $R_2$ and $R_4$ are different and denote hydrogen or an unsubstituted alkyl group having 1 to 8 carbon atoms, preferably methyl or ethyl.

8. A 1,10-Diaminodecane of the formula Ia

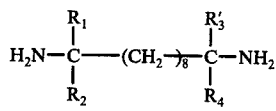

wherein $R_1$, $R_2$, $R'_3$ and $R_4$ are identical, and represent alkyl, cycloalkyl, aralkyl, phenyl, naphthyl, or $R_1$ and $R_2$ and/or $R_3$ and $R_4$ conjointly with the carbon atom to which they are linked, form a 5-membered to 12-membered alkylene or oxaalkylene ring.

9. 1,10-Diaminodecanes of the formula Ia according to claim 8, wherein $R_1$ and $R_2$ and/or $R'_3$ and $R_4$, conjointly with the carbon atom to which they are linked, form an unsubstituted 5-membered to 12-membered alkylene ring or an unsubstituted 5-membered or 6-membered oxaalkylene ring.

10. The compound 1,10-diethyl-1,10-dimethyl-1,10-diaminodecane.

11. Process for the manufacture of 1,10-diaminodecanes of the formula Ia

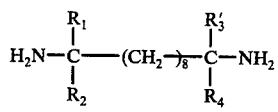

wherein $R_1$ represents an alkyl, cycloalkyl, aralkyl, phenyl or naphthyl group, $R'_3$ represents an alkyl, cycloalkyl, aralkyl or naphthyl group which corresponds to $R_3$, or represents a phenyl group and $R_2$ and $R_4$ independently of one another represent hydrogen or an alkyl, cycloalkyl, aralkyl, phenyl or naphthyl group, or $R_1$ and $R_2$ and/or $R'_3$ and $R_4$, conjointly with the carbon atom to which they are linked, form a 5-membered to 12-membered alkylene or oxaalkylene ring, characterised in that a compound of the formula

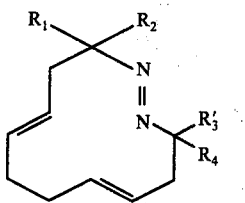

wherein what has been indicated under formula Ia applies to $R_1$, $R_2$, $R'_3$ and $R_4$, is hydrogenated in the presence of an inert organic solvent, by catalytic means, in one or two stages and with the reaction temperature being raised to at least 120° C, to give a compound of the formula Ia.

12. Process according to claim 11, characterised in that, in a first stage, a compound of the formula II is hydrogenated at a temperature below 150° C to give a compound of the formula III

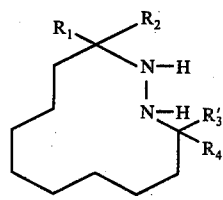

and the compound of the formula III is then hydrogenated at elevated temperature and preferably with the addition of ammonia, to give a compound of the formula Ia.

13. Process according to claim 11, for the manufacture of 1,10-diaminodecanes of the formula I, wherein $R_2$ and $R_4$ each represent hydrogen, characterised in that a compound of the formula II, wherein $R_2$ and $R_4$ each denote hydrogen and what has been indicated under formula Ia applies to $R_1$ and $R'_3$, is hydrogenated in one stage at a temperature of at least 120° C.

14. Process according to claim 11, characterised in that the compound of the formula II which is employed is one in which $R_1$ and $R'_3$ are identical and represent an alkyl group having 1 to 8 carbon atoms or a 1-nuclear cycloalkyl group having 6 to 8 ring carbon atoms, and wherein $R_2$ and $R_4$ are different and denote hydrogen or an alkyl group having 1 to 8 carbon atoms, preferably methyl or ethyl.

* * * * *